(12) United States Patent
Mulier

(10) Patent No.: US 10,702,307 B2
(45) Date of Patent: Jul. 7, 2020

(54) MULTI-CANNULA SURGICAL INSTRUMENT

(71) Applicant: Vesalius Medical Technologies BVBA, Hoegaarden (BE)

(72) Inventor: Kristoffel Pieter Maria Mulier, Hoegaarden (BE)

(73) Assignee: Vesalius Medical Technologies BVBA, Hoegaarden (BE)

( * ) Notice: Subject to any disclaimer, the term of this patent is extended or adjusted under 35 U.S.C. 154(b) by 301 days.

(21) Appl. No.: 14/784,910

(22) PCT Filed: Apr. 15, 2014

(86) PCT No.: PCT/EP2014/057653
§ 371 (c)(1),
(2) Date: Oct. 15, 2015

(87) PCT Pub. No.: WO2014/170338
PCT Pub. Date: Oct. 23, 2014

(65) Prior Publication Data
US 2016/0143662 A1 May 26, 2016

(30) Foreign Application Priority Data
Apr. 17, 2013 (EP) .................................... 13164090

(51) Int. Cl.
*A61B 17/34* (2006.01)
*A61B 18/14* (2006.01)
*A61B 18/00* (2006.01)

(52) U.S. Cl.
CPC ...... *A61B 17/3496* (2013.01); *A61B 18/1482* (2013.01); *A61B 18/1487* (2013.01);
(Continued)

(58) Field of Classification Search
CPC . A61B 17/3474; A61B 17/3496; A61B 18/14; A61B 18/1482; A61B 18/1487;
(Continued)

(56) References Cited

U.S. PATENT DOCUMENTS 5,401,247 A 3/1995 Yoon
5,637,096 A 6/1997 Yoon
(Continued)

FOREIGN PATENT DOCUMENTS

WO WO/2002/085444 A1 10/2002

OTHER PUBLICATIONS

International Search Report dated May 27, 2014.

*Primary Examiner* — Michael F Peffley
*Assistant Examiner* — Khadijeh A Vahdat
(74) *Attorney, Agent, or Firm* — Wallenfelt Law PLC

(57) ABSTRACT

A multi-cannula surgical instrument (1), having an inner cannula (3) movably disposed within an outer cannula (2), the inner cannula (3) having a blunt distal tip (3*b*), one or more first inner ducts (31) and one or more first flow-through orifices (32) arranged to allow one or more fluid flows therethrough, where the inner and the outer cannula (2, 3) at the proximal ends (2*a*, 3*a*) thereof are mounted onto a hub (4) that includes a biasing mechanism (43) coupled to the inner cannula (3) and arranged to bias the inner cannula (3) automatically from a retracted towards an advanced position in case of absence of resistance against the inner cannula (3), where the outer cannula (2) has one or more second flow-through orifices (22) that are in fluid communication with one or more second ducts (21) arranged between the outer and the inner cannula (2, 3), where the second flow-through orifices (22), the hub (4) and the second duct(s) (21) are configured to allow at least one fluid flow therethrough.

20 Claims, 6 Drawing Sheets

(52) U.S. Cl.
CPC ...... *A61B 18/1492* (2013.01); *A61B 17/3474* (2013.01); *A61B 2018/00577* (2013.01); *A61B 2018/00595* (2013.01)

(58) Field of Classification Search
CPC ........ A61B 18/1492; A61B 2018/0077; A61B 2018/00595
USPC .................................................... 606/41–50
See application file for complete search history.

(56) References Cited

U.S. PATENT DOCUMENTS

| | | |
|---|---|---|
| 6,063,081 A | 5/2000 | Mulier et al. |
| 6,905,489 B2* | 6/2005 | Mantell .............. A61B 17/3496 600/3 |
| 2006/0079873 A1* | 4/2006 | Scopton ......... A61B 17/320016 606/37 |
| 2006/0089633 A1 | 4/2006 | Bleich et al. |
| 2012/0209167 A1 | 8/2012 | Weber et al. |

* cited by examiner

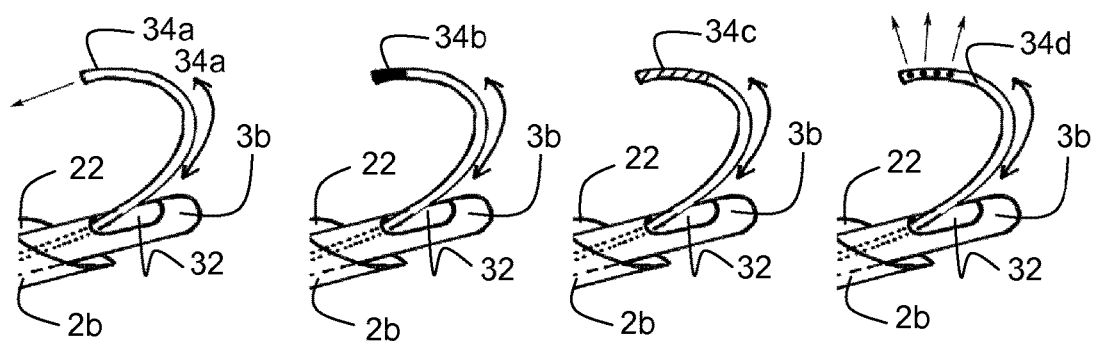
FIG. 13a  FIG. 13b  FIG. 13c  FIG. 13d
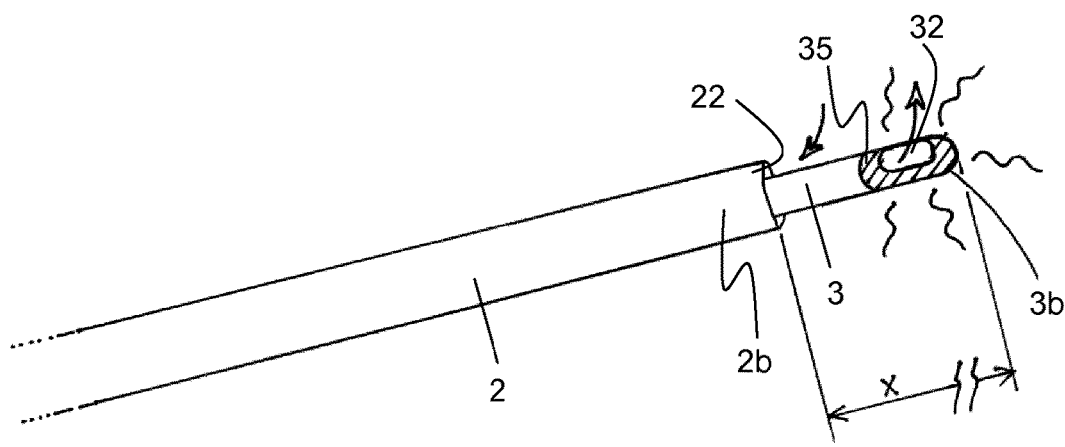
FIG. 14

MULTI-CANNULA SURGICAL INSTRUMENT

This application claims the benefit of European patent application No. 13164090.6 filed Apr. 17, 2013, which is hereby incorporated by reference in its entirety.

FIELD OF THE INVENTION

The present invention generally relates to a multi-cannula surgical instrument. The invention relates in particular to a multi-cannula surgical instrument in the form of a multi-cannula safety needle or a multi-cannula electrocautery instrument.

The multi-cannula surgical instrument according to the invention more specifically comprises a rigid outer cannula, comprising a proximal end and a distal tip. This multi-cannula surgical instrument furthermore comprises an inner cannula, comprising a proximal end and a blunt distal tip arranged to hamper penetration of tissue and/or to prevent involuntary damage of tissue by said distal tip of said inner cannula. Said inner cannula further comprises one or more first inner ducts and one or more first flow-through orifices near said distal tip of said inner cannula, said first flow-through orifice(s) being in fluid communication with said first inner duct(s). Fluids include gases as well as liquids. Said first inner duct(s) and said first flow-through orifice(s) are configured to allow one or more fluid flows therethrough. Said outer cannula at least partially surrounds said inner cannula and said inner cannula is movably disposed within said outer cannula between a retracted position, wherein said distal tip of said outer cannula is positioned beyond said distal tip of said inner cannula concealing said blunt distal tip of said inner cannula, and an advanced position, wherein said blunt distal tip of said inner cannula is positioned beyond said distal tip of said outer cannula concealing said distal tip of said outer cannula. This multi-cannula surgical instrument further comprises a hub mounting said inner and said outer cannula at said proximal ends thereof. Said hub comprises a biasing mechanism that is coupled to said inner cannula and that is arranged to bias said inner cannula automatically from said retracted towards said advanced position in case of absence of resistance against said inner cannula.

A cannula is defined as a hollow tube that is insertable into a human or animal body.

BACKGROUND OF THE INVENTION

An electrocautery instrument is a surgical instrument that is used to heat tissue with electricity. Electrocauterization (or electrocautery) is a safe procedure that is routinely used in surgery to remove unwanted or harmful tissue. It can also be used to burn and seal blood vessels, which helps reduce or stop bleeding. A small probe with an electric current running through it is used to burn or destroy the tissue. A grounding pad is placed on the body (usually the thigh) before the surgery to protect the patient from the harmful effects of the electricity.

In U.S. Pat. No. 6,063,081, an electrocautery instrument is described that is configured with a hollow electrode/blade disposed within a retractable suction tube. The suction tube is slidably disposed partially within an internal lumen of a handle and projects distally out of the end thereof. The suction tube is adapted to slide proximally and distally with respect to the handle and electrode/blade by means of a sliding lever extending out of a slot in the handle. With the suction tube in a retracted position, a distal portion of the electrode/blade projects beyond the distal tip of the tube, such that electrocautery can be performed. With the suction tube in an advanced position, the suction tube completely conceals the tip of the electrode/blade. The hollow electrode/blade has a source of conductive fluid coupled to the proximal end thereof. This conductive fluid is expelled from the distal (blade) end of the hollow electrode/blade during electrocautery. The conductive fluid emanating from the electrode/blade conducts the RF electrocautery energy away from the blade so that it is primarily the fluid, rather than the metal blade, which actually accomplishes cutting/cauterisation of the treated tissue.

The disadvantage of this type of electrocautery instruments is that the suction tube has to be moved manually with respect to the handle and the electrode/blade using a handle.

A safety needle is a needle having a protected sharp tip to prevent inadvertent tissue contact.

The oldest and most traditional safety needle was developed in 1932 by Janos Veress and is called a Veress needle. Such a conventional Veress needle comprises an outer, preferably tubular, cannula with a sharp tip or point in order to allow piercing or penetration of the tissue forming the wall of an anatomical structure or an anatomical cavity. The force required to penetrate this wall is dependent upon the type and the thickness of the tissue of this wall. Once this wall has been penetrated, it is desirable to protect this sharp tip of the outer cannula to prevent inadvertent contact with tissue in the anatomical structure or further tissue forming the wall of this anatomical structure or anatomical cavity. Particularly, when a substantial force is needed to pierce through this wall, once this wall has been pierced, a problem could appear in that the sharp tip travels too far into the anatomical structure or cavity because of lack of further tissue resistance causing inadvertent injury of tissue and/or the wall of the same or other anatomical structures or anatomic cavities. Therefore, preferably an inner, preferably tubular, cannula with a blunt tip is provided which is pushed in the shaft of the outer cannula when a direct pressure is exerted on the blunt tip, as when penetrating the wall of the anatomical structure of cavity, and which automatically emerges out of the outer cannula once the wall of the tissue has been pierced. In order to be able to automatically emerge out of the outer cannula, the inner cannula is attached internally to a spring mechanism. Accordingly, when this Veress needle is pushed with its blunt tip against the wall that has to be pierced, the blunt tip retracts allowing the sharp end of the Veress needle to pierce this wall. Once the Veress needle has pierced through this wall, the Veress needle no longer encouters any resistance and the blunt end which is attached to the internal spring re-emerges to protect the anatomical structure from inadvertent puncture.

The safety of this Veress needle consequently is a big advantage thereof. A further big advantage thereof is the inherent physical feedback of the Veress needle, i.e. by hearing and sensing a 'click' when the inner cannula emerges out of the outer cannula after that the wall of the anatomical structure or anatomical cavity to be treated has been penetrated, hence informing the surgeon.

Until now however, these Veress needles only have a limited use and can only be applied in one way fluid applications, such as abdominal access techniques for laparoscopy, wherein $CO_2$ is inserted through the Veress needle to inflate the space creating a pneumoperitoneum, and minimal invasive surgery.

Other examples of safety needles can be found in U.S. Pat. Nos. 5,401,247 and 5,637,096.

Also these safety needles have the disadvantage that they do not allow a simultaneous flow of two or more fluids throughout the different cannulas of this needle.

Known solutions that could provide multi-flow applications, such as catheters, then require several steps for insertion and still have to be inserted using a separate sharp needle which can harm an inner anatomical structure that does not need to or may not at all be penetrated.

An additional disadvantage of catheters that are made out of plastic is that they become weak when they are subjected to excessive heat.

International patent application WO 02/085444 entitled "Laparoscopic Insertion Device" describes an instrument for laparoscopic surgery that comprises an outer cannula 86 with outer cannula orifices 84, an annular wall 90 that is silver soldered to the outer cannula 86 to form a first channel for fluids, an inner cannula 88 with inner cannula orifices 94, and an obturator 38 with blunt distal tip 38 that must be removed in order to enable the inner cannula to form a second channel for fluids. In FIG. 6 of WO 02/085444, the laparoscopic insertion device is shown in a retracted position. In FIG. 4 of WO 02/085444, the laparoscopic insertion device is shown in an advanced position. A hub with spring 44 is arranged to bias the laparoscopic insertion device in the advanced position in absence of resistance.

The laparoscopic device known from WO 02/085444 is limited in use and has several disadvantages. First, it is a fairly large device with an outer diameter of 0.203 inches (see page 8, lines 14-18) or 5.16 mm which cannot be pierced through tissue. Inserting the laparoscopic device known from WO 02/085444 consequently requires an incision. The laparoscopic device known from WO 02/085444 in other words cannot be used as a needle that is pierced through tissue. Furthermore, because of the many parts, including a.o. an obturator 38, an annular wall 90, an O-ring seal 48, etc., the laparoscopic device of WO 02/085444 cannot be scaled down to obtain the diameter of a needle that can be pierced through tissue as this would reduce the effective space for fluids and consequently the achievable flow rates unacceptably.

As a result of the presence of the annular wall 90 that is silver soldered to the outer cannula 86 to form a first channel for fluids and the obturator 38, the space between the inner cannula and outer cannula is non-optimal.

In order to use the inner cannula as a second channel for fluids, the obturator must be removed during the surgery. The obturator must be unthreaded and thereafter retracted in order to be removed. Unthreading and retracting the obturator introduces a risk for damaging tissue surrounding the tip of the insertion device. While removing the obturator, the inner cannula may exercise a suction force on surrounding tissue. The inner cannula consequently cannot be used to remove fluids/gasses since there is a risk that tissue or a cavity wall becomes adhered to the tip of the inner cannula as a result of the suction force. Moreover, once the obturator is removed, internal space is in open communication with external space through the inner cannula. Fluids may escape from the inner space increasing the risk for contamination.

Consequently, there exists a need to provide a multi-cannula surgical instrument according to the preamble of the first claim allowing a simultaneous multi-flow (inflow, outflow or a combination thereof) of fluids throughout the multi-cannula surgical instrument. Such a multi-cannula surgical instrument which is designed to allow a simultaneous in- and outflow for instance can be used to flush an anatomical cavity.

A further need is to provide such a multi-purpose multi-cannula surgical instrument that is employable as an electrocautery instrument as well as a safety needle, more preferably wherein a minimum number of parts have to be altered to perform another functionality.

There further exists a need to provide such a multi-cannula surgical instrument which is easy to use and easy to manipulate during the surgical act.

In case of an electrocautery instrument, there furthermore exists a need to provide an electrocautery instrument wherein no manual manipulation is necessary to move the inner cannula within the outer cannula. The suction of fumes, fluids and debris is a function of the distance of the outer and inner cannula and the tissue. Manual manipulation is slow, cumbersome and always a compromise.

In case of a safety needle, it is furthermore a need to provide a multi-cannula surgical instrument which has the safety characteristics of a Veress needle, i.e. reducing the danger to unintentionally penetrate tissue that has not to be penetrated or that may not be penetrated. There furthermore exists a need to provide a safety needle that is applicable in a broader application field than the known Veress and safety needles. It is also a need to replace the existing catheters in areas where undesired harming of tissue is possible due to the mandatory insertion of a needle in the body to introduce the catheter into the body.

SUMMARY OF THE INVENTION

The invention thereto provides in a multi-cannula surgical instrument according to the preamble of the first claim, wherein said outer cannula comprises one or more second flow-through orifices at said distal tip thereof, and said multi-cannula surgical instrument comprises one or more second ducts arranged between said inner cannula and said outer cannula, said second duct(s) being in fluid communication with said one or more second flow-through orifices and said second duct(s), said one or more second flow-through orifices and said hub being configured to allow at least one fluid flow throughout said hub, said second duct(s) and said one or more second flow-through orifices.

Such a multi-cannula surgical instrument first of all allows simultaneous multiple fluid flows throughout said inner and outer cannula and in, out of, or a combination thereof, said flow-through orifices.

Because of the presence of a blunt distal tip of the inner cannula and the biasing mechanism, the multi-cannula surgical instrument can on the one hand be used as a safety needle, more specific a Veress needle, since, when the distal tip of the outer cannula is sharp in order to be able to penetrate tissue, this sharp distal tip of the outer cannula is concealed by the blunt distal tip of the inner cannula in the advanced position of the inner cannula, in this way hampering penetration of tissue and/or preventing involuntary damage of tissue.

On the other hand, the multi-cannula surgical instrument can be used as an electrocautery instrument by accommodating the blunt distal tip of the inner cannula with one or more cauterizing or ablating electrodes.

Consequently, a multi-cannula surgical instrument is obtained which can be used to perform two different functions and allows to alter a limited number of parts to enable the other function to be performed.

Because of the fact that the outer cannula is rigid, a user using this multi-cannula surgical instrument is not faced with the problems the user is confronted with using a flexible catheter, i.e. that first of all, a plurality of different manipulations has to be performed to introduce the catheter into the human or animal body, and that secondly, the catheter easily bends when manipulating it and when being faced to heat.

In a preferred embodiment of an according to the invention, said biasing mechanism comprises at least one resilient element that is coupled with said inner cannula and that is arranged to resiliently bias said inner cannula from said retracted towards said advanced position when the resistance against said inner cannula diminishes.

In case the multi-cannula surgical instrument is used as an electrocautery instrument, the abovementioned resilient element allows a quicker and more accurate regulation of the amount of aspiration of the smoke, fluids (blood as well as saline) or debris produced during the electrocauterization process, as well as a more accurate dosing of the fluid or gas used during the electrocauterization process.

This resilient element more preferably is a spring.

In an advantageous embodiment of a multi-cannula surgical instrument according to the invention, said hub comprises a distance adjustment mechanism that is arranged to manually adjust the position of said blunt distal tip of said inner cannula beyond said distal tip of said outer cannula.

In a favorable embodiment of a multi-cannula surgical instrument according to the invention, at least said inner cannula comprises a side wall being provided with a scale which is arranged to measure the position of said inner cannula with respect to said outer cannula.

In an advantageous embodiment of a multi-cannula surgical instrument according to the invention, said multi-cannula surgical instrument comprises one or more spacing elements being
  located within said second duct(s);
  configured to maintain said outer and said inner cannula at a constant distance with respect to each other; and
  configured to allow one or more fluid flows throughout said second duct(s).

In order to prevent occlusion or to promote irrigation, said outer cannula comprises a side wall provided with one or more additional second flow-through orifices.

In a possible embodiment of a multi-cannula surgical instrument according to the invention, said outer and inner cannula both are bent. This allows reaching for places that a straight cannula cannot reach.

Said inner cannula also can comprise a plurality of inner ducts and comprises for each inner duct at least one flow-through orifice near said blunt distal tip being in fluid communication with each respective inner duct, wherein said inner ducts and said flow-through orifices are configure to allow a plurality of fluid flows throughout said plurality of inner ducts and said flow-through orifices.

In an optional embodiment of a multi-cannula surgical instrument according to the invention, said inner cannula comprises a nozzle arranged at said distal blunt end, said nozzle comprising a plurality of small flow-through orifices being in fluid communication with said one or more first inner ducts.

Said multi-cannula surgical instrument furthermore can comprise one or more guides that are inserted in said inner cannula and are extending through one or more of said first flow-through orifices.

Another possibility is that said multi-cannula surgical instrument comprises a balloon which is insertable in an anatomic cavity or an anatomical tubular structure and which is applied over said one or more first flow-through orifices near said blunt distal tip of said inner cannula, wherein one or more of said first flow-through orifice(s) are configured to inflate said balloon using a gas and/or to fill said balloon using a liquid.

In a possible embodiment of a multi-cannula surgical instrument according to the invention, said multi-cannula surgical instrument is arranged as a safety needle comprising an outer cannula with a sharp distal tip arranged to allow penetration of human and/or animal tissue, wherein in said advance position of said inner cannula, said inner cannula is positioned beyond said sharp distal tip of said outer cannula hampering penetration of tissue and/or preventing involuntary damage of tissue by said sharp distal tip of said outer cannula.

In a possible embodiment of a multi-cannula surgical instrument according to the invention, said blunt distal tip of said inner cannula is enlarged in view of the remaining part of said inner cannula.

The advantage thereof is that after penetration, the risk of involuntary damage or penetration of tissue with the sharp distal tip of the outer cannula is seriously reduced.

In another possible embodiment of a multi-cannula surgical instrument according to the invention, said multi-cannula surgical instrument is arranged as an electrocautery instrument having an inner cannula having a blunt distal tip provided with one or more cauterizing or ablating electrodes.

BRIEF DESCRIPTION OF THE DRAWINGS

FIG. 8b illustrates a perspective top view of an insert as used in the safety needle as shown in FIG. 7a;

FIG. 10b illustrates a cross section according to line C-C through the distal part of the safety needle ash shown in FIG. 10a;

FIG. 13a illustrates a perspective front view of a blunt distal tip of a safety needle according to the invention having an inner cannula into which a guide is inserted which is arranged with an optical fibre at the end thereof;

FIG. 13b illustrates a perspective front view of a blunt distal tip of a safety needle according to the invention having an inner cannula into which a guide is inserted having a sensor at the end thereof;

FIG. 13c illustrates a perspective front view of a blunt distal tip of a safety needle according to the invention having an inner cannula into which a guide is inserted having an electrically conductive wire that can be applied for ablation purposes at the end thereof;

FIG. 13d illustrates a perspective front view of a blunt distal tip of a safety needle according to the invention having an inner cannula into which a guide is inserted having a hollow tube that can transport liquid or gas for optimal distribution at the end thereof;

FIG. 14 illustrates a perspective front view of the distal part of an electrocautery instrument according to invention having an inner cannula with a cauterising/ablating electrode on the blunt distal tip thereof, wherein the position of the blunt distal tip with the electrode is manually adjustable with respect to the outer cannula.

DETAILED DESCRIPTION OF EMBODIMENT(S)

Figure 1:
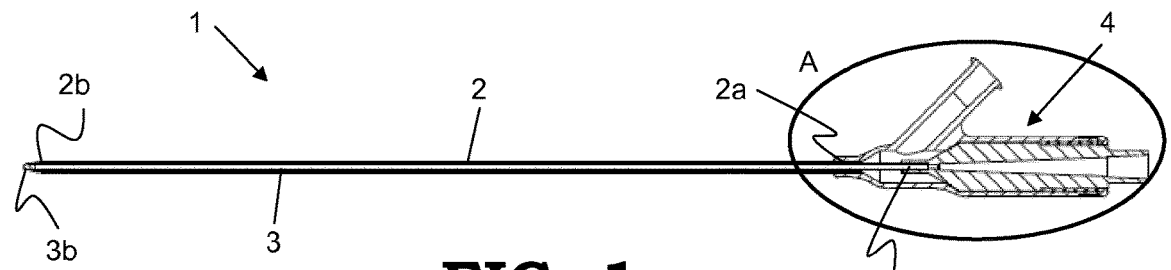
FIG. 1 illustrates a cross section of an exemplary embodiment of a safety needle according to the invention.

As shown in the figures, the multi-cannula surgical instrument (1) according to the invention comprises a hollow, preferably tubular, inner and outer cannula (2, 3). In some (patent) literature, instead of the term cannula, the term lumen is used. The outer cannula (2) is formed out of a rigid material. Depending on the surgical application, the outer cannula (2) is manufactured out of stainless steel or a rigid plastic material, the material of this outer cannula (2) however not being limited thereto and possible consisting out of any suitable material. Depending on the application, the inner cannula (3) is manufactured out of a rigid material such as the ones mentioned before, but can also be manufactured out of a flexible material such as a flexible plastic material or any other flexible material suitable therefore.

The outer cannula (2) has a shaft into which the inner cannula (3) at least partially extends. In other words, the outer cannula (2) at least partially surrounds the inner cannula (3). The inner cannula (3) thus has a smaller diameter than the outer cannula (2). The outer and the inner cannula (2, 3) possibly are coaxially arranged with respect to each other.

The outer cannula (2) has a distal tip (2b) and a proximal end (2a). The inner cannula (3) has a blunt distal tip (3b) and a proximal end (3a).

Figure 6:
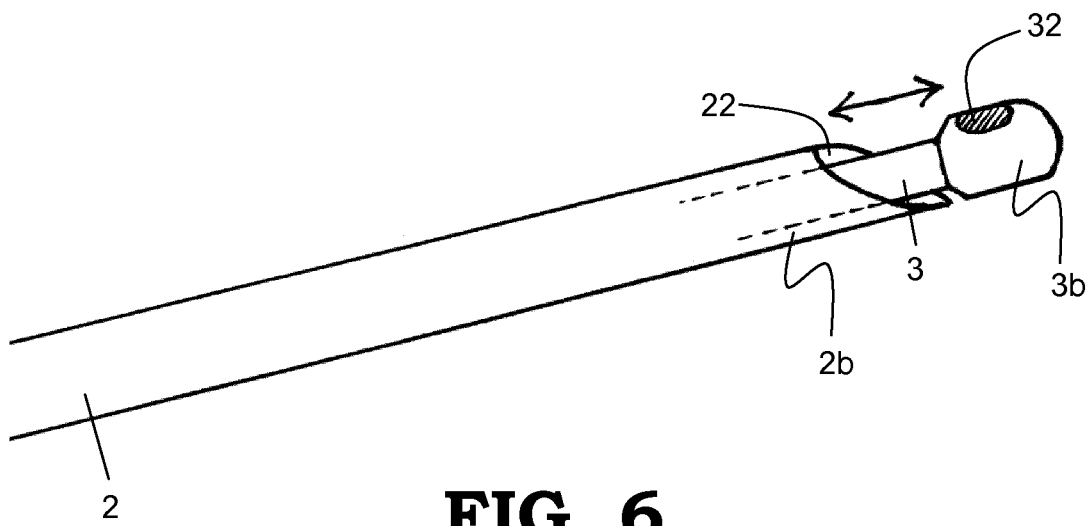
FIG. 6 illustrates a perspective front view of a distal part of a safety needle according to the invention having an inner cannula with an enlarged blunt distal tip with respect to the remainder part of the inner cannula.
Figure 7:
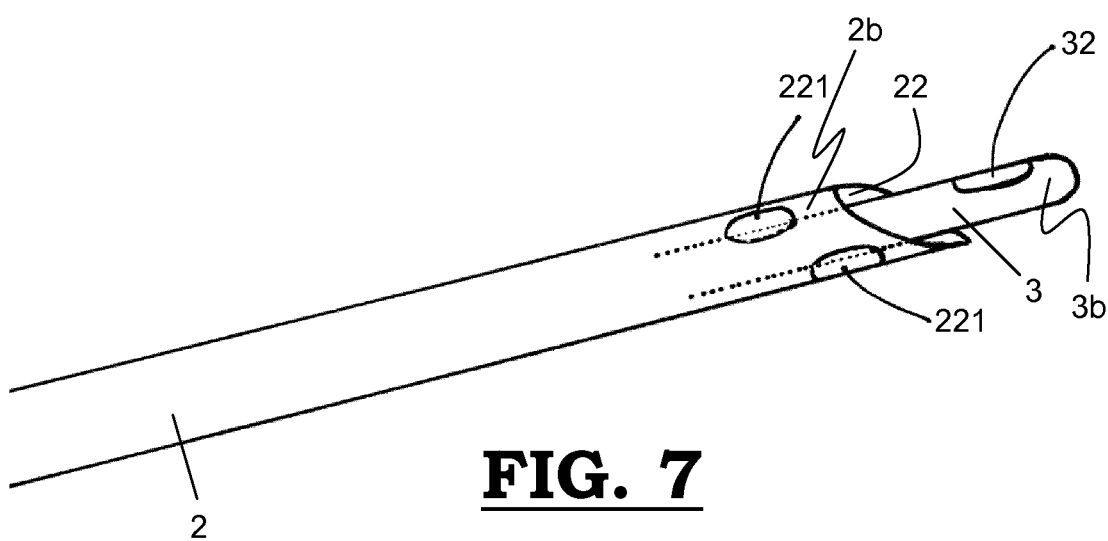
FIG. 7 illustrates a perspective front view of a distal part of a safety needle according to the invention having an outer cannula with several flow-through orifices in the side wall thereof.

The inner cannula (3) has one or more first inner ducts (31) which are configured to allow a fluid flow therethrough. A fluid includes a gas as well as a liquid. The inner cannula (3) furthermore has one or more flow-through orifices (32) near its blunt distal tip (3a) through which fluid can pass, these flow-through orifices (32) being in fluid communication with a respective inner duct (31). Between the outer and the inner cannula (2, 3), one or more second inner ducts (21) are arranged that are configured to allow a fluid flow therethrough. These one or more second inner ducts (21) thus are situated within the shaft of the outer cannula (2). The outer cannula (2) has one or more second flow-through orifices (22) near its distal tip (2a) through which fluid can pass, these flow-through orifices (22) being in fluid communication with the one or more second inner ducts (21). The multi-cannula surgical instrument (1) as shown in FIGS. 1, 2, 6, 7, 8a, 8d, 9, 10a, 11, 12, 13a-13d and 14 all comprise one second flow-through orifice (22) which is arranged at the distal tip (2b) of the outer cannula (2). The multi-cannula surgical instrument (1) as shown in FIG. 6 comprises one second flow-through orifice (22) at the distal tip (2b) of the outer cannula (2), and a plurality of second flow-through orifices (221) arranged near the distal tip (2b) in the wall of the outer cannula (2).

As can be seen in FIGS. 1, 2, 3 and 5, the multi-cannula surgical instrument (1) comprises a hub (4) mounting the inner and outer cannula (2, 3) at the proximal ends (2a, 3a) thereof. This hub (4) preferably is manufactured out of a plastic material. The hub (4) comprises an inner coupling element (44) that at its distal end (44a) is connected to the proximal end (3a) of the inner cannula (3). This distal end (44a) more specifically surrounds the proximal end (44a) of the inner cannula (3). This coupling element (44) houses a first inner duct (41) which is in fluid communication with the first inner duct(s) (31) of the inner cannula (3). The hub (4) furthermore comprises an outer part (45) to which the proximal end (2a) of the outer cannula (2) is connected. This distal end (45a) more specifically surrounds the proximal end (3a) of the outer cannula (2). This outer part (45) houses one or more second inner ducts (42) which are in fluid communication with the second inner duct(s) (21) located in the shaft of the outer cannula (2). Between the coupling element (44) and the outer part (45) of the hub (4), preferably a sealing ring (46) is arranged to prevent leakage of fluid out between the outer part (45) and the coupling element (44).

The multi-cannula surgical instrument (1) further comprises a biasing mechanism (43) that is coupled to the coupling part (44) of the hub (4). This biasing mechanism allows the coupling element (44) to reciprocally move within the outer part (45) of the hub (4). This biasing mechanism furthermore is arranged to automatically bias the coupling element (44) towards the distal end (45a) of the outer part (45). Because the inner cannula (3) at its proximal end (3a) is coupled to the distal end (44a) of this coupling element (4), also the inner cannula (3) is reciprocally movable within the shaft of the outer cannula (2). This inner cannula (23) therewith is movable between a retracted, wherein the distal tip (2b) of the outer cannula (2) is positioned beyond the blunt distal tip (3b) of the inner cannula (3) concealing this blunt distal tip (3b), and an advanced position, wherein the blunt distal tip (3b) of the inner cannula (3) is positioned beyond the distal tip (2b) of the outer cannula (2) concealing this distal tip (2b) of the outer cannula (2). Because of the biasing mechanism, a direct pressure on the blunt distal tip (3b) pushes the inner cannula (3) into the shaft of the outer cannula (2). When the blunt distal tip (3b) encounters no more resistance, the blunt distal tip (3b) automatically returns from the retracted to the advanced position. In other words, when the blunt distal tip (3b) is pulled away from the point of resistance, the blunt distal tip (3b) springs forward and protrudes in front of the distal tip (2b) of the outer cannula (2).

Figure 3:
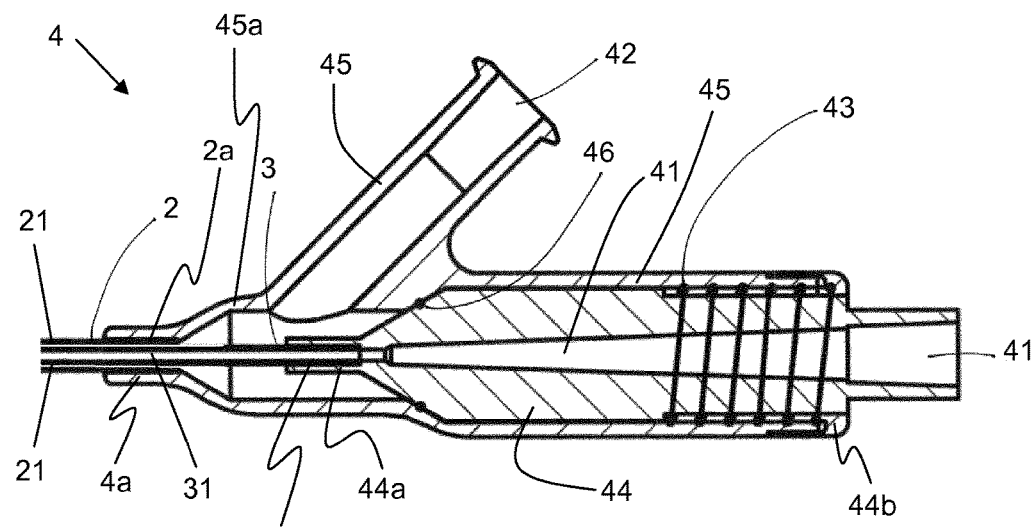
FIG. 3 illustrates a detail of the encircled part A as shown in FIG. 1.
Figure 4:
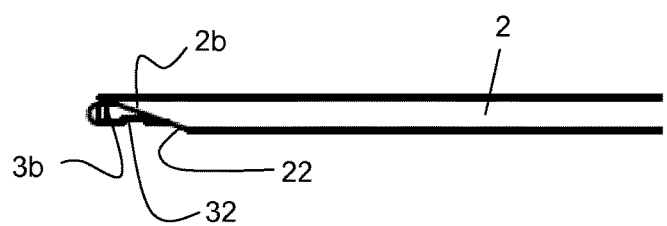
FIG. 4 illustrates a detail B of the encircled part B as shown in FIG. 2.

The biasing mechanism is specifically arranged in the form of a resilient element and more specifically in the form of a spring (43). This biasing mechanism preferably is mounted at the proximal end (44b) of the coupling element (44). In the embodiment as shown in FIG. 3, a helical or coil spring (43) is mounted around this proximal end (44b). This helical or coil spring (43) is mounted in compression between the inner coupling element (44) and the outer part (45) of the hub (4). The blunt distal tip (3b) of the inner cannula (3) thus is movable against the helical or coil spring (43) within the shaft of the outer cannula (2). The inner cannula (3) thus is reciprocally movable within the outer cannula (2) in a resilient way. Consequently, the inner cannula (3) resiliently moves within the outer cannula (2) when the resistance against the blunt distal tip (3b) of the inner cannula (3) changes. In other words, the inner cannula (3) is resiliently biased from the retracted to the advanced position when the resistance against the blunt distal tip (3b) of the inner cannula (3) diminishes.

Figure 5:
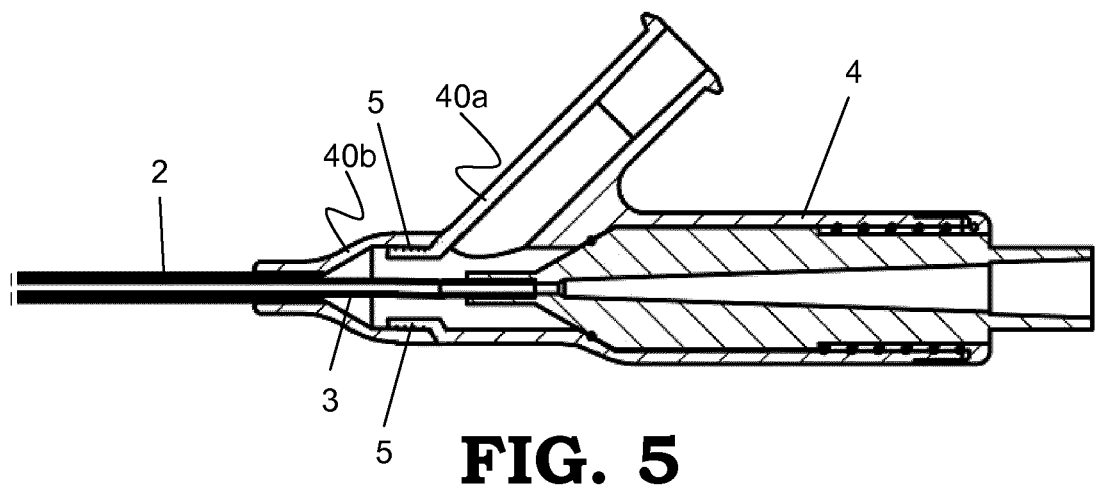
FIG. 5 illustrates a detail B of the encircled part B as shown in FIG. 2, wherein the hub comprises a fixed part and a movable part.

As shown in FIG. 5, the hub (4) can comprise a distance adjustment mechanism that is arranged to manually adjust the distance the blunt distal end (3b) of the inner cannula (3) extends beyond the distal tip (2b) of the outer cannula (2). This distance adjustment mechanism for instance can be configured as the hub (4) being built out of a fixed part (40a) and a movable part (40b). As can be seen in FIG. 5, this fixed and movable part (40a, 40b) preferably are provided with screw thread (5). By turning the movable part (40b) with relation to the fixed part (40a), the outer cannula (3) moves with relation to the inner cannula (2) through which the distance the blunt distal end (3b) of the inner cannula (3) is extending beyond the distal tip (2b) of the outer cannula (2) is adjusted. At least the inner cannula (3) can therewith be provided with a (metric) scale (of measurement) (not shown on the figures) to measure the position of the inner cannula (3) with respect to the outer cannula (2).

Figure 2:
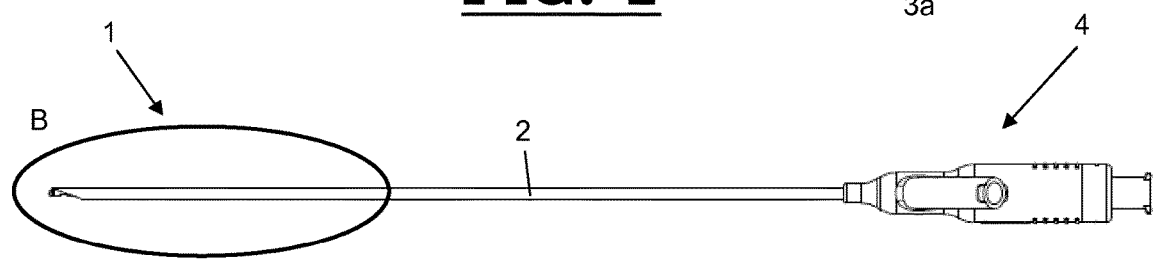
FIG. 2 illustrates a top view of the exemplary embodiment of the safety needle as shown in FIG. 1.

In the FIGS. 1 and 2, a multi-cannula surgical instrument in the form of a safety needle (1) is shown. In the FIGS. 4, 6, 7, 8a, 8d, 9, 10a and 11, 12, 13a-13d and 14, the distal end of a safety needle (1) is shown. A safety needle (1) typically comprises an outer cannula (2) having a sharp distal tip (2b) that is arranged to pierce (also called puncture or penetrate) tissue, more specifically tissue forming the wall of an anatomical (also called pathological or body) cavity (not shown in the figures) or anatomical tubular structure. The tissue to be penetrated can be the tissue of a closed anatomical cavity, such as amongst others abdomen, small blood vessels such as veins and arteries, epidural, pleural and subarachnoid spaces, heart ventricles and spinal, synovial cavities, cysts and bursas. The tissue to be penetrated however can also be any other type of tissue of an anatomical structure such tissue of lung, uterine, bladder, intestines, stomach, liver, etc. This distal tip (2b) of the outer cannula (2) therewith preferably terminates at a peripheral edge disposed in a plane positioned at an acute angle relative to the longitudinal axis of the outer cannula (2). Because of the biasing mechanism (43) as described above, more specifically the presence of the spring (43), the inner cannula (3) automatically (resiliently) moves from its retracted to its advanced position after the sharp distal end (2b) of the outer cannula (2) has pierced the tissue and the blunt distal end (3b) of the inner cannula (3) no longer encounters resistance of tissue in order to prevent the sharp distal tip (2b) of the outer cannula (2) to further penetrate tissue or to involuntary damage tissue by this sharp distal tip (2b).

The outer cannula (2) therewith has a diameter and a wall thickness that is dependent upon the procedure to be performed and the anatomical structure or anatomical cavity that has to be penetrated. The material of this inner and outer cannula (2, 3) also depends on the application of the safety needle. The material however of the outer cannula (2) typically is stainless steel to allow accurate penetration of tissue. Also the inner cannula is preferably manufactured out of stainless steel, but could for economic reasons also be manufactured out of a plastic material.

Figure 11:
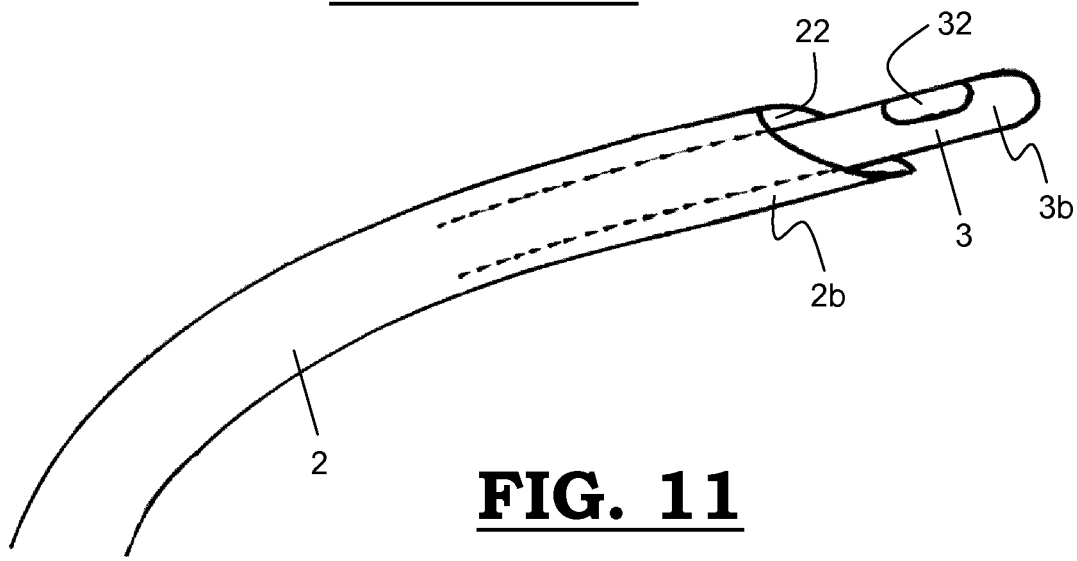
FIG. 11 illustrates a perspective front view of a safety needle according to the invention having a bent inner and outer cannula.

In case of a bent safety needle (1), as shown in FIG. 11, the outer cannula (2) typically is manufactured out of stainless steel, while the inner cannula (3) is typically manufactured out of a flexible material such as a flexible plastic material in order to allow that the inner cannula (3) to be movable within the outer cannula (2) as described above.

In the embodiment as shown in FIG. 6, the blunt distal tip (3b) of the inner cannula (3) is enlarged with respect to the remainder part of the inner cannula (3).

Figure 8A:
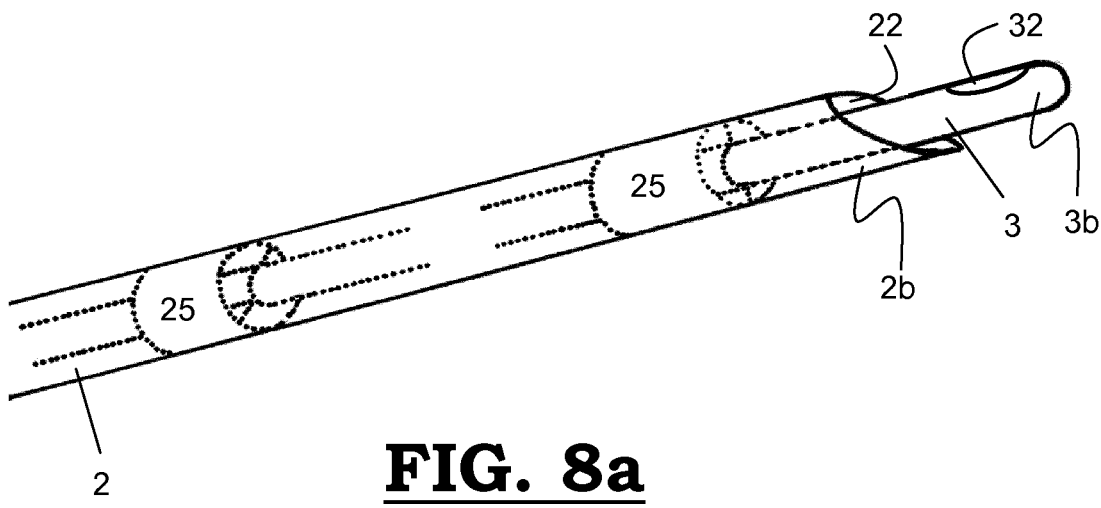
FIG. 8a illustrates a perspective front view of a distal part of a safety needle according to the invention having inserts at a certain distance from each other in the duct between the outer and the inner cannula.
Figure 8B:
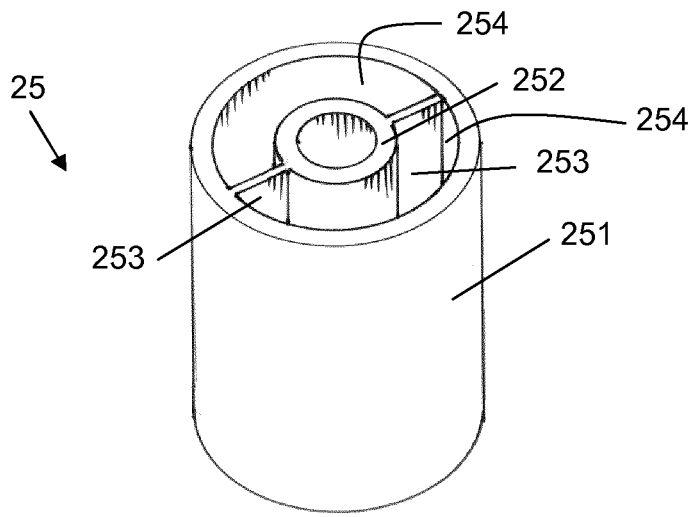
Figure 8C:
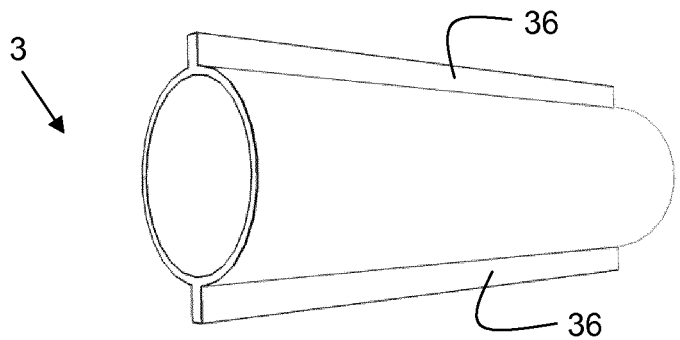
FIG. 8c illustrates a perspective front view of an inner cannula having two spacing ribs disposed opposite one another and extending in the length of the inner cannula.
Figure 8D:
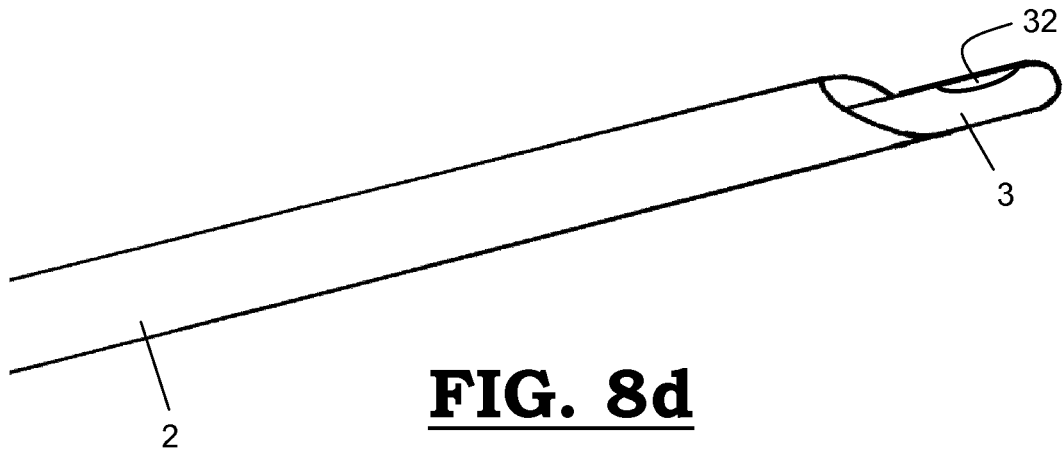
FIG. 8d illustrates a perspective front view of a distal part of a safety needle according to the invention, wherein the inner cannula lies against one side of the outer cannula.

In order to maintain the outer and the inner cannula (2, 3) at a constant distance from each other, and optionally to maintain the outer and the inner cannula (2, 3) concentrically with respect to one another, the multi-cannula surgical instrument (1) comprises one or more spacing elements. In a first possible embodiment, these spacing elements consist out of one or more inserts (25) that are arranged in the second inner ducts (21) between the outer and the inner cannula (2, 3). In the embodiment as shown in FIG. 8a, two such inserts (25) are positioned at a mutual distance with respect to one another. As can been seen in FIG. 8b, such an insert (25) preferably consists of a tubular hollow outer part (251) that abuts the inner wall of the outer cannula (2) and a tubular hollow inner part (252) that abuts the outer wall of the inner cannula (3). Between this tubular hollow outer and inner part (251, 252), one or more in the length of the inner cannula (3) extending spacing ribs (253) are arranged to maintain this outer and inner part (251, 252) at a constant distance from each other, or optionally to maintain this outer and inner part (251, 252) concentrically with respect to one another. The spaces (254) present between the tubular hollow outer and inner parts (251, 252) allow fluid flow throughout the insert (25). In a second embodiment as shown in FIG. 8c, the spacing elements consist of spacing ribs (36) of equal or different size, extending from the outer surface of the inner cannula (3) up to the inner surface of the outer cannula (2) and extending in the length direction of the inner cannula (3). In the embodiment as shown in FIG. 8c, two such ribs (36) of equal size are arranged which are disposed opposite each other each at a different side of the inner cannula (3) through which the outer and the inner cannula (2, 3) are concentrically arranged with respect to one another. When two ribs (36) of different size are provided, for instance one large and one very small spacing rib (36), or when providing only one spacing rib (36), the inner cannula (3) lies closer to one side of the outer cannula (2) or in the latter case lies against one side of the outer cannula (2) (see FIG. 8d), through which the outer and the inner cannula (2, 3) are not concentrically arranged with respect to one another. The arrangement as shown in FIG. 8d has the advantage that the inner cannula (3) is situated very close to the sharp side of the sharp distal tip (2b) of the outer cannula (2) through which the blunt distal end (3b) of the inner cannula (3) is better shielded against the sharp side of the outer cannula (2). Such an inner cannula (3) preferably is manufactured out of a plastic material.

Figure 9:
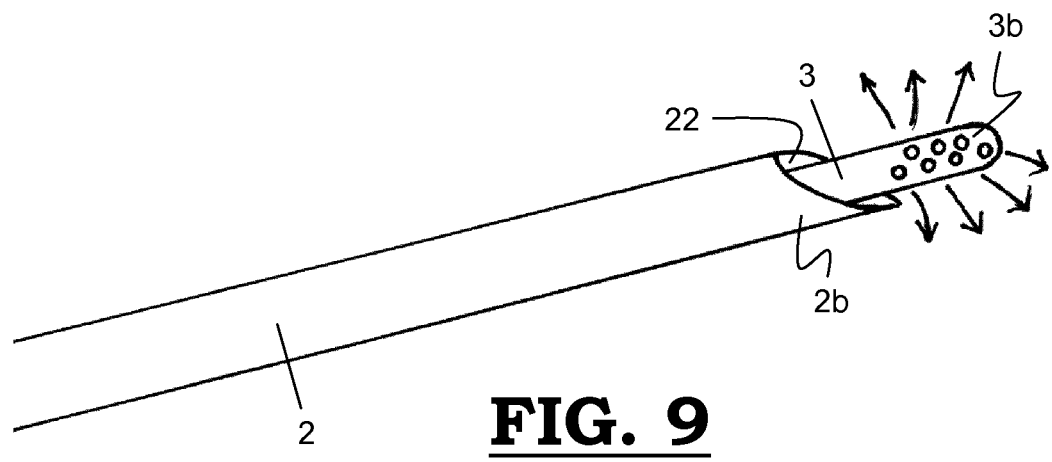
FIG. 9 illustrates a perspective front view of a distal part of a safety needle according to the invention having a nozzle at the blunt distal tip of the inner cannula.

In the embodiment as shown in FIG. 9, the blunt distal tip (3b) of the inner cannula (3) is provided with a nozzle consisting of a plurality of small flow-through orifices (222) being in fluid communication with said one or more first inner ducts (21).

Figure 10A:
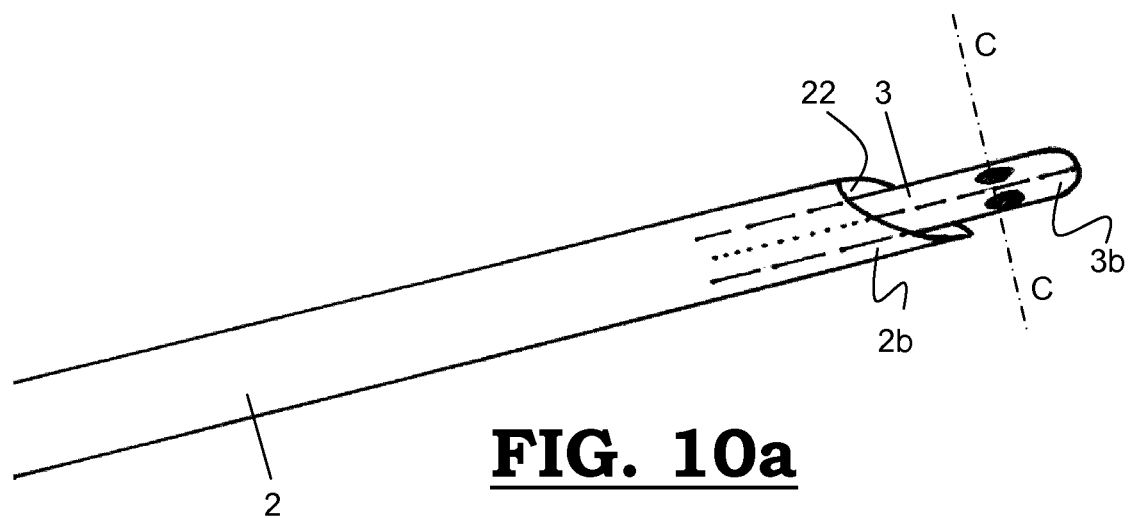
FIG. 10a illustrates a perspective front view of the distal part of a safety needle according to the invention having an inner cannula split-up in two longitudinal parts, each having being in fluid or gas communication with a respective flow-through orifice.
Figure 10B:
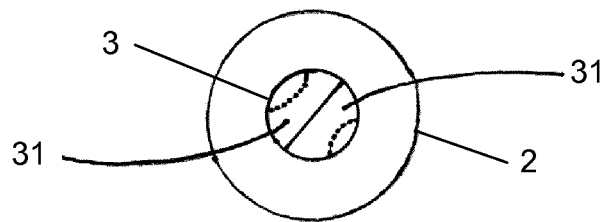

In the embodiment as shown in FIG. 10a, and as can be seen in FIG. 10b, the inner cannula (3) is subdivided in a plurality of first inner ducts (31). For each first inner duct (31), at least one, and in this embodiment one, first flow-through orifice (32) is provided.

Figure 12:
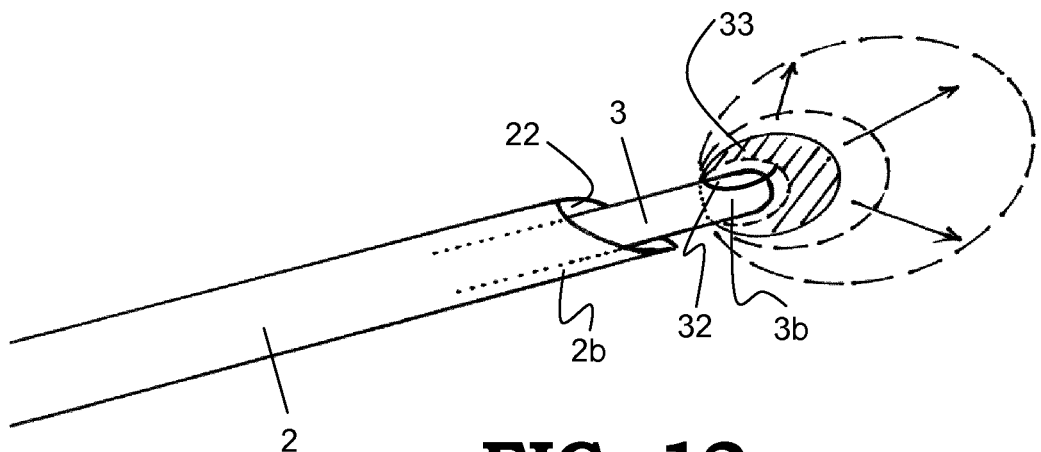
FIG. 12 illustrates a perspective front view of a blunt distal tip of a safety needle according to the invention having an inner cannula configured to accommodate a balloon that is insertable into an anatomic cavity or an anatomic tubular structure and that is inflatable with a gas or fillable with a fluid.

In the embodiment as shown in FIG. 12, a balloon (33) that is insertable in an anatomical cavity or an anatomical tubular structure such as a vein (not shown in the figures) is applied over one or more of the first flow-through orifices (32) near the blunt distal tip (3b) of the inner cannula (3). This balloon (33) is inflatable using a gas or is fillable using a liquid that passes through the one or more first flow-through orifices (32) over which the balloon (33) is applied.

In the embodiments as shown in FIGS. 13a, 13b, 13c and 13d, one or more guides (34a-34d) are inserted in the one or more first inner ducts (31) of the inner cannula (3) and are extending through the one or more first flow-through orifices (32) of the inner cannula (3). In FIG. 13a, the guide (34a) is arranged with an optical fibre at the end thereof. In FIG. 13b, a guide (34b) is inserted having a sensor at the end thereof. In FIG. 13c, a guide (34c) is inserted having an electrically conductive wire that can be applied for ablation purposes at the end thereof. In FIG. 13d, a guide (34d) is inserted having a hollow tube that can transport and spray a fluid for optimal distribution at the end thereof.

In FIG. 14, a multi-cannula surgical instrument (1) in the form of an electrocautery instrument is shown. The distal tip (2b) of the outer cannula (2) typically is blunt in order to avoid involuntary penetration of harming of tissue such as skin or in other tissue exposed during an open surgery procedure. For minimal invasive surgery, the distal tip (2b) of the outer cannula (2) however may also be executed sharp. The blunt distal tip (3b) of the inner cannula (3) typically comprises a cauterizing or ablating electrode (35). The position of the blunt distal tip (3b) of the inner cannula (3) with respect to the outer cannula (2) is manually adjustable. In other words, the distance (X) between the blunt distal tip (3b) of the inner cannula (3) and the distal tip (2b) of the outer cannula (2) is manually adjustable using a distance adjustment mechanism as already described above. When the hub (4) is provided with a resilient biasing mechanism (43) as described above, a user using this electrocautery instrument (1) is able to push the inner cannula (3) shallower or deeper into the outer cannula (2) allowing to automatically aspirate more or less smoke, fluids or debris produced during the electrocauterization process Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A multi-cannula surgical instrument for treating a bursa, comprising:
    a rigid outer cannula comprising a proximal end and a sharp distal tip sized to penetrate a bursa;
    an inner cannula comprising:
        a proximal end and an integral rounded blunt distal tip arranged to hamper penetration of tissue and/or to prevent involuntary damage of tissue by said blunt distal tip without an obturator,
        one or more first inner ducts and one or more first flow-through orifices near said blunt distal tip, said one or more first flow-through orifices being in fluid communication with said one or more first inner ducts, said one or more first inner ducts and said one or more first flow-through orifices being configured to allow one or more fluid flows therethrough;
    wherein said rigid outer cannula at least partially surrounds said inner cannula and said inner cannula is movably disposed within said rigid outer cannula between a retracted position, in which said distal tip of said rigid outer cannula is positioned beyond said blunt distal tip concealing said blunt distal tip and an advanced position in which said blunt distal tip is positioned beyond said distal tip of said rigid outer cannula; and
    a hub mounting said inner cannula and said rigid outer cannula at said proximal ends of said inner cannula and said rigid outer cannula, said hub comprising a biasing mechanism being coupled to said inner cannula and being arranged to bias said inner cannula automatically from said retracted position towards said advanced position in case of absence of resistance against said inner cannula,
    wherein said rigid outer cannula comprises one or more second flow-through orifices at said distal tip thereof, and said multi-cannula surgical instrument comprises one or more second ducts situated within said rigid outer cannula and arranged between said inner cannula and said rigid outer cannula, said one or more second ducts including a fluid path that fluidly contacts said inner cannula and being in fluid communication with said one or more second flow-through orifices, said one or more second flow-through orifices and said hub being configured to allow at least one fluid flow through said hub, said one or more second ducts and said one or more second flow-through orifices.

2. The multi-cannula surgical instrument according to claim 1, wherein said biasing mechanism comprises at least one resilient element that is coupled with said inner cannula and that is arranged to resiliently bias said inner cannula from said retracted position towards said advanced position when the resistance against said inner cannula diminishes.

3. The multi-cannula surgical instrument according to claim 2, wherein said resilient element is a spring.

4. The multi-cannula surgical instrument according to claim 1, wherein said hub comprises a distance adjustment mechanism that is arranged to manually adjust the position of said blunt distal tip of said inner cannula beyond said sharp distal tip of said rigid outer cannula.

5. The multi-cannula surgical instrument according to claim 1, wherein said inner cannula comprises a side wall being provided with a scale which is arranged to measure the position of said inner cannula with respect to said rigid outer cannula.

6. The multi-cannula surgical instrument according to claim 1, wherein said multi-cannula surgical instrument comprises one or more spacing elements being
 located within said one or more second ducts;
 configured to maintain said outer and said inner cannula at a constant distance with respect to each other; and
 configured to allow one or more fluid flows throughout said one or more second ducts.

7. The multi-cannula surgical instrument according to claim 1, wherein said rigid outer cannula comprises a side wall, wherein the side wall comprises one or more of the second flow-through orifices.

8. The multi-cannula surgical instrument according to claim 1, wherein said outer and inner cannula both are bent.

9. The multi-cannula surgical instrument according to claim 1, wherein said one or more first inner ducts of said inner cannula comprise a plurality of inner ducts and said one or more first flow-through orifices comprise a plurality of first flow-through orifices near said blunt distal tip such that each of said plurality of inner ducts is in fluid communication with at least one of said plurality of first flow-through orifices to allow one of said one or more fluid flows therethrough.

10. The multi-cannula surgical instrument according to claim 1, wherein said inner cannula comprises a nozzle arranged at said distal blunt end, said nozzle comprising a plurality of small flow-through orifices being in fluid communication with said one or more first inner ducts.

11. The multi-cannula surgical instrument according to claim 1, wherein said multi-cannula surgical instrument comprises one or more guides that are configured to be inserted in said inner cannula and that are configured to be extended through one or more of said one or more first flow-through orifices.

12. The multi-cannula surgical instrument according to claim 1, wherein said multi-cannula surgical instrument comprises a balloon which is insertable in an anatomic cavity or an anatomic tubular structure and which is applied over said one or more first flow-through orifices arranged near said blunt distal tip of said inner cannula, and wherein said one or more first flow-through orifices are configured to inflate said balloon using a gas and/or to fill said balloon with a liquid.

13. The multi-cannula surgical instrument according to claim 1, wherein said blunt distal tip of said inner cannula is enlarged in view of the remaining part of said inner cannula.

14. The multi-cannula surgical instrument according to claim 1, wherein said blunt distal tip of the inner cannula is provided with a cauterizing or ablating electrode.

15. The multi-cannula surgical instrument according to claim 1, wherein an interior of the blunt distal tip of the inner cannula is in fluid communication with said one or more first flow-through orifices.

16. A multi-cannula surgical instrument, comprising:
 a rigid outer cannula comprising a proximal end and a sharp distal tip sized to pierce tissue;
 an inner cannula comprising:
  a proximal end and an integral rounded blunt distal tip arranged to hamper penetration of tissue or to prevent involuntary damage of tissue by said blunt distal tip,
  a first inner duct and one or more first flow-through orifices near said blunt distal tip, said one or more first flow-through orifices being in fluid communication with said first inner duct, said first inner duct and said one or more first flow-through orifices being configured to allow one or more fluid flows therethrough;
 wherein said rigid outer cannula at least partially surrounds said inner cannula and said inner cannula is movably disposed within said rigid outer cannula between a retracted position, in which said distal tip of said rigid outer cannula is positioned beyond said blunt distal tip concealing said blunt distal tip and an advanced position in which said blunt distal tip is positioned beyond said distal tip of said rigid outer cannula; and
 a hub mounting said inner cannula and said rigid outer cannula at said proximal ends of said inner cannula and said rigid outer cannula, said hub comprising a biasing mechanism being coupled to said inner cannula and being arranged to bias said inner cannula automatically from said retracted position towards said advanced position in case of absence of resistance against said inner cannula,
 wherein said rigid outer cannula comprises one or more second flow-through orifices at said distal tip thereof, and said multi-cannula surgical instrument comprises a second duct that is situated within said rigid outer cannula and arranged between said inner cannula and said rigid outer cannula, said second duct including a fluid path that fluidly contacts said inner cannula and being in fluid communication with said one or more second flow-through orifices and said hub, said one or more second flow-through orifices and said hub being configured to allow at least one fluid flow through said hub, said second duct and said one or more second flow-through orifices.

17. The multi-cannula surgical instrument of claim 16, wherein said second duct is defined by an inner wall of the outer cannula and an outer wall of the inner cannula.

18. The multi-cannula surgical instrument of claim 17, further comprising a spacing element disposed within said second duct and arranged to maintain the outer cannula and the inner cannula at a constant distance from each other.

19. The multi-cannula surgical instrument of claim 16, wherein said inner cannula is disposed within said second duct.

20. A multi-cannula surgical instrument, comprising:
a rigid outer cannula comprising:
- a proximal end and a sharp distal tip sized to pierce tissue;
- a wall connecting the proximal end to the distal tip and forming a hollow tube; and
- a second inner duct disposed within the hollow tube;

an inner cannula that is at least partially disposed within the second inner duct of the rigid outer cannula, the inner cannula comprising:
- a proximal end and a blunt distal tip arranged to hamper penetration of tissue or to prevent involuntary damage of tissue by said blunt distal tip,
- a first inner duct and one or more first flow-through orifices near said blunt distal tip, said one or more first flow-through orifices being in fluid communication with said first inner duct, said first inner duct and said one or more first flow-through orifices being configured to allow one or more fluid flows therethrough;

wherein said rigid outer cannula at least partially surrounds said inner cannula and said inner cannula is movably disposed within said rigid outer cannula between a retracted position in which said distal tip of said rigid outer cannula is positioned distally beyond said blunt distal tip, and an advanced position in which said blunt distal tip is positioned distally beyond said distal tip of said rigid outer cannula; and a hub mounting said inner cannula and said rigid outer cannula at said proximal ends of said inner cannula and said rigid outer cannula, said hub comprising a biasing mechanism being coupled to said inner cannula and being arranged to bias said inner cannula automatically from said retracted position towards said advanced position in case of absence of resistance against said inner cannula, wherein said rigid outer cannula comprises one or more second flow-through orifices at said distal tip thereof, said second duct being in fluid communication with said one or more second flow-through orifices and said hub, said one or more second flow-through orifices and said hub being configured to allow at least one fluid flow through said hub, said second duct and said one or more second flow-through orifices.

* * * * *